United States Patent [19]

Clark et al.

[11] 4,424,276

[45] Jan. 3, 1984

[54] METHOD AND APPARATUS FOR MEASURING THE GASEOUS CONTENT OF BLOOD

[75] Inventors: Justin S. Clark; Ming-Cheng Yen, both of Salt Lake City, Utah

[73] Assignee: Intermountain Health Care, Salt Lake City, Utah

[21] Appl. No.: 327,756

[22] Filed: Dec. 7, 1981

[51] Int. Cl.³ ............................................. G01N 33/48
[52] U.S. Cl. ...................................... 436/50; 204/1 T; 204/403; 422/68; 422/81; 436/68; 436/134; 436/138; 436/150
[58] Field of Search ................. 23/230 B, 928; 422/68, 422/81; 128/635; 204/195 B, 1 T; 436/68, 134, 138, 150, 50, 52

[56] References Cited

U.S. PATENT DOCUMENTS

| | | | |
|---|---|---|---|
| 3,271,111 | 9/1966 | Boyd, Jr. et al. | 422/81 X |
| 3,639,829 | 2/1972 | Harnoncourt | 422/75 X |
| 3,658,478 | 4/1972 | Spergel et al. | 422/81 |
| 3,874,850 | 4/1975 | Sorensen et al. | 23/928 X |
| 3,950,137 | 4/1976 | Larson et al. | 422/81 |
| 3,992,151 | 11/1976 | Vanderhoeden | 23/230 A X |
| 4,221,567 | 9/1980 | Clark et al. | 23/928 X |

Primary Examiner—Arnold Turk
Attorney, Agent, or Firm—Thorpe, North & Western

[57] ABSTRACT

Method and apparatus for determining the gaseous content of a diluent, such as determining the oxygen or carbon dioxide content of blood. A sample of the diluent whose gaseous content is to be measured is anaerobically pumped past a junction tee after being placed in a reservoir. A second diluent, not part of the sample, is equilibrated with a gas (not the gas to be measured) in a first tonometer. This second equilibrated diluent is pumped past the junction tee where it is mixed with the diluent sample. The gas in the second diluent is selectively chosen to drive the gas to be measured into the dissolved phase. The diluent mixture is then allowed to flow through an appropriate sensor that senses the presence of the gas to be measured. This first measurement is stored in a suitable controller, such as a microprocessor. The controller, after causing the system to be flushed of all traces of the diluent sample, prepares a mixture of two selected diluents, such as first and second saline solutions, one of which is equilibrated in a tonometer to have 0% of the gas to be measured therein, and the other of which is equilibrated in another tonometer to have a known percent of the gas to be measured therein. The controller selectively controls the flow rates at which these two diluents are mixed, typically under the constraint that the flow rate of the mixture through the sensor is the same as was used in obtaining the first sensor measurement, until a second sensor measurement is obtained that is the same as the first sensor measurement. The gaseous content of the diluent sample may then be calculated based upon known physical measurements, such as flow rates, barometric pressure, and temperature.

27 Claims, 3 Drawing Figures

METHOD AND APPARATUS FOR MEASURING THE GASEOUS CONTENT OF BLOOD

BACKGROUND OF THE INVENTION

This invention relates to a method and system for measuring the gaseous content of a fluid medium, and more particularly to an improved polarographic method and system that is especially well suited for measuring the oxygen or carbon dioxide content of blood.

Before discussing the prior art and the invention herein disclosed, it will be helpful to define the following terms. These terms will be used throughout this application and, unless noted otherwise, will be defined as indicated.

gaseous content—that amount of a specified gas that is physically dissolved in a given fluid medium, such as a water based diluent. The accurate measurement of the gaseous content of a specified fluid medium is one of the objectives of the present invention.

equilibrated solution—a solution in contact with a specified gas of a given partial pressure that has the specified gas dissolved therein to the point of equilibrium (i.e., the solution has absorbed the gas to such a degree that no further gas of the specified type at the given partial pressure, may be dissolved therein).

tonometer—a device for causing a solution flowing therethrough to become equilibrated with a gas that is injected therein. (See U.S. Pat. No. 4,221,567, items 18 and 19, for a simplified description of a tonometer.)

anaerobically—performed in the absence of air or oxygen. Thus, an anaerobic pump is one that pumps a solution through a desired tube or conduit without causing air or oxygen to be introduced thereinto.

A simple method and system for the accurate and quick determination of the gaseous content of a fluid medium, such as the oxygen or carbon dioxide content of blood, has been long sought for by chemical analysts, particularly those in the medical field.

Several methods are known in the art to perform such measurements, but all these prior art methods suffer from one or more drawbacks. Perhaps the best known method, and the accepted standard for measuring oxygen content in blood, is the manometric method, introduced by Van Slyke and Neill in 1924. In the manometric method, oxygen is chemically released from hemoglobin and extracted in a vacuum space where it is brought to a chosen volume. The total pressure of this volume is measured. The oxygen is then chemically removed from the gas phase. The total pressure of the gas phase with the oxygen removed therefrom is remeasured and subtracted from the previous measurement. The volume at standard conditions corresponding to this pressure difference is calculated using the standard gas laws. The manometric method is quite reproducible. However, it has been criticized because:

(1) it takes an excessive amount of time for each oxygen measurement (about 15 minutes);
(2) the procedure is very tedious; and
(3) extensive skill and experience is required by those performing the measurement.

In about 1961, the Galvanic method was developed and was specifically directed toward eliminating the shortcomings of the Van Slyke manometric method. The Galvanic method uses a galvanic cell to reduce the oxygen which has been driven out of the blood into the gas phase. Because the reduction process of the galvanic cell is specific to oxygen, the integral of the galvanic cell is a direct measure of the total oxygen reduced. In theory, if all the blood oxygen were reduced by the galvanic cell, the method would be at least as good, and perhaps better than, the manometric method. However, in practice design constraints have not permitted a galvanic cell that will reduce all of the oxygen. Further, the integrated output of the galvanic cell is dependent upon the rate of oxygen delivery to the cell, thereby introducing another source of error into the measurement. Thus, the method relies on calibrations and must accept the systematic differences which can exist between calibration and measurement.

Another method known in the art for measuring the oxygen content of blood is the polarographic method. This method was first introduced in 1940. However, its practical implementation had to await the membrane covered polarographic sensor developed by Clark in 1956. The polarographic method differs in principle from both the manometric and galvanic methods in that the oxygen, rather than being driven chemically from the hemoglobin into the gas phase for measurement, is instead driven from the hemoglobin into a water-based diluent where it exists as physically dissolved oxygen. The blood oxygen content is therefore directly determined from the concentration of physically dissolved oxygen which is measured by a polarographic electrode.

The polarographic method was developed, as was the galvanic method, as an improved alternative to the slow and tedious Van Slyke manometric method. Indeed, the polarographic method may make an oxygen content determination in much less time than the Van Slyke method. Analysis times have been reported between three to six minutes. Further, less tediousness is involved in the polarographic method, and there is also less operator dependence. However, the accuracy of measurements made therewith is dependent upon the calibration of the oxygen electrode (as is the case with the galvanic method). Such methods must accept, therefore, the possibility of systematic differences between calibration and measurement.

Further, prior art methods, such as those described above, typically require an operator to carefully and skillfully meter out a prescribed sample size. The transfer of this sample between the metering apparatus and the measuring apparatus creates a risk of sample contamination, which contamination may adversely impact the accuracy of the measurement to be made. Such contaminations are caused principally by "end contaminations" created through the withdrawing and inserting of the sample fluid through devices such as a needle syringe. These end contaminations, unfortunately, become mixed in with the pool where the entire sample is housed within the syringe or similar device.

OBJECTS AND SUMMARY OF THE INVENTION

In view of the above limitations of known methods and systems for determining the oxygen content of blood, it is a primary object of the present invention to provide an improved method and system for determining the gaseous content of a fluid medium that eliminates or minimizes the shortcomings associated with such prior art methods and systems.

Specifically, it is an object of the present invention to provide a method and system for measuring the oxygen content of blood that is reproducible, quickly performed, and that does not rely upon the skill or expertise of the operator performing the measurement.

A further object of the present invention is to provide such a method and system whose accuracy is not dependent upon the calibration of a particular sensor, such as an oxygen or carbon dioxide sensor.

A still further object of the present invention is to provide a method and system for determining the gaseous content of a fluid medium wherein there are no systematic differences between calibration and measurement.

Another object of the present invention is to provide such a method and system for measuring the gaseous content of a fluid medium where there is no requirement for an operator to meter out a specific sample size.

Still another object of the present invention is to provide a method and system as above described that eliminates the possibility of contamination of the sample during its delivery to the measuring apparatus.

Another object of the present invention is to provide a method and system of measuring the gaseous content of a fluid medium, such as blood, that is entitled to first principle status, i.e., to provide a method that involves only physical measurements and constants.

The above objects are realized in a preferred embodiment that measures, for example, the oxygen content of blood by injecting a blood sample into a reservoir and anaerobically pumping this sample past one input port of a junction tee. A first saline solution, equilibrated with a gas that is not oxygen (carbon monoxide) is also anaerobically pumped past the other port of the junction tee. The output fluid exiting the output port of the junction tee is thus a blood/saline mixture in which the oxygen in the blood hemoglobin is driven out by the carbon monoxide into the dissolved phase. The ratio of saline to blood within this mixture is equal to the ratio of the volumetric fluid flow of the saline solution to the volumetric fluid flow of the blood sample.

The mixture thus formed is then directed into an appropriate oxygen sensor at a volumetric fluid flow rate that is equal to the sum of the respective flow rates of the saline solution and blood sample. These flow rates are known or can be measured and recorded. The sensor response of the blood/saline mixture corresponding to the middle portion of the mixture (to avoid contaminations associated with the end portions of the mixture) at the known flow rate is then recorded. This sensor response is referred to hereafter as the first sensor response. A suitable controller (that controls the flow rates of fluids that pass through the junction tee) then prepares a saline mixture sample that, when passed through the sensor under the same flow rate conditions, produces a second sensor response that is the same as the first sensor response.

The above process is accomplished by preparing a second saline solution that is equilibrated with oxygen. This second saline solution is anaerobically pumped through the reservoir and junction tee, pushing all end traces of the previous blood sample thereout as waste material, at a controlled volumetric flow rate F2. The first saline solution, equilibrated with carbon monoxide (and therefore containing 0% oxygen) is also anaerobically pumped through the junction tee at a controlled volumetric flow rate F1. The saline mixture thus formed is directed to the sensor at a flow rate equal to F1 plus F2. The rates F1 and F2 are selectively controlled by the controller so that their sum is typically constant, equal to the known flow rate of the blood/saline mixture used in obtaining the first sensor response. However, the individual flow rates F1 and F2 are selectively adjusted by the controller (under the constraint that their sum is constant) until the same sensor response is produced as the first sensor response. Because the second saline solution is equilibrated with 100% oxygen, and the first saline solution is equilibrated with a gas (carbon monoxide) that guarantees 0% oxygen, the ratio of oxygen present in the combined saline mixture is merely the ratio of F2 to F1 plus F2. A relatively straight forward calculation can then be used to determine the oxygen content of the saline mixture based upon the flow rates F1 and F2. In turn, this calculated oxygen content will be the same as the oxygen content of the blood/saline mixture inasmuch as the sensor response to both solutions is identical.

The above procedure may be used equally well for determining the gaseous content of any fluid where the gas to be measured is something other than oxygen, if a suitable means is used to drive the gas to be measured into the dissolved phase (assuming it is chemically bonded within the solution, as is oxygen to hemoglobin in blood).

The apparatus of the present invention that is employed to carry out the above-described procedure includes two sources of saline solution, or an equivalent water-based diluent, each of which is coupled through separate feed tubes or lines to respective input ports of a junction tee. Interposed between the sources of saline solution and the junction tee in each line are a pump and a tonometer. The pump anaerobically controls the flow rate of the saline or other solution that is withdrawn from the solution source and directs the solution to the junction tee through the tonometer. The tonometer, in turn, allows a desired gas to be dissolved to the point of equilibrium within the solution. One of the lines or tubes includes an in-line reservoir in which a specified quantity of fluid may be held prior to reaching the junction tee. A suitable injection port is provided in this line immediately before the reservoir so that a suitable sample, such as a blood sample, could be inserted into the reservoir. Once a sample is thus inserted, the saline solution will push the sample through the junction tee and remaining parts of the system at a flow rate determined by the pump connected to that particular line.

The output port of the junction tee is connected to another line or tube which is coupled, preferrably through a mixing coil, to an appropriate sensor adapted to sense the presence of a particular gas dissolved in the fluid mixture to which the sensor is exposed.

A suitable controller is coupled to the sensor and pump of each line. This controller controls the flow rates associated with each pump. It also stores or records the sensor response to the blood/saline mixture that is initially caused to flow through the sensor. In the preferred embodiment, the controller is further programmed, or otherwise adapted, to automatically adjust the flow rates of their respective saline solutions until the same sensor response is attained with the mixture of equilibrated saline solutions as was obtained with the blood/saline mixture. The controller also records the appropriate flow rates and performs the necessary calculations in order to give an indication of the oxygen, or other gas, content of the blood or other fluid.

The invention may be expanded to include multiple lines, more than two, each of which has its respective pump, tonometer, and source of saline solution (or equivalent) associated therewith. Further, the sensor employed with such an expanded system is adapted to sense a plurality of gases, rather than a single gas. Through selective control of the flow rates in each line, including the stopping of flow and the reversing of the direction of flow through a given tonometer, it is possible to measure the gas content of a plurality of gases within a given fluid sample as part of a single measurement process. In addition to the gaseous content of the sample, the capacity of the fluid sample with respect to a particular gas may also be measured. From these measurements, other useful parameters may be readily calculated automatically by the controller as part of the same measurement. For example, if the fluid sample were blood, in addition to being able to measure the oxygen and carbon dioxide content of a given blood sample, one could also measure the oxygen capacity of the sample, the hemoglobin available in the sample for gas exchange, and the oxygen saturation level of the sample.

BRIEF DESCRIPTION OF THE DRAWINGS

The above objects, features, and advantages of the present invention will be more apparent from the following more detailed discussion presented in connection with the accompanying drawings, in which.

DETAILED DESCRIPTION OF THE INVENTION

While the invention herein described is described in terms of measuring the oxygen content of blood, it is to be understood that the method could be used to measure the gaseous content of any suitable fluid medium or matrix in which the gas is dissolved.

Figure 1:
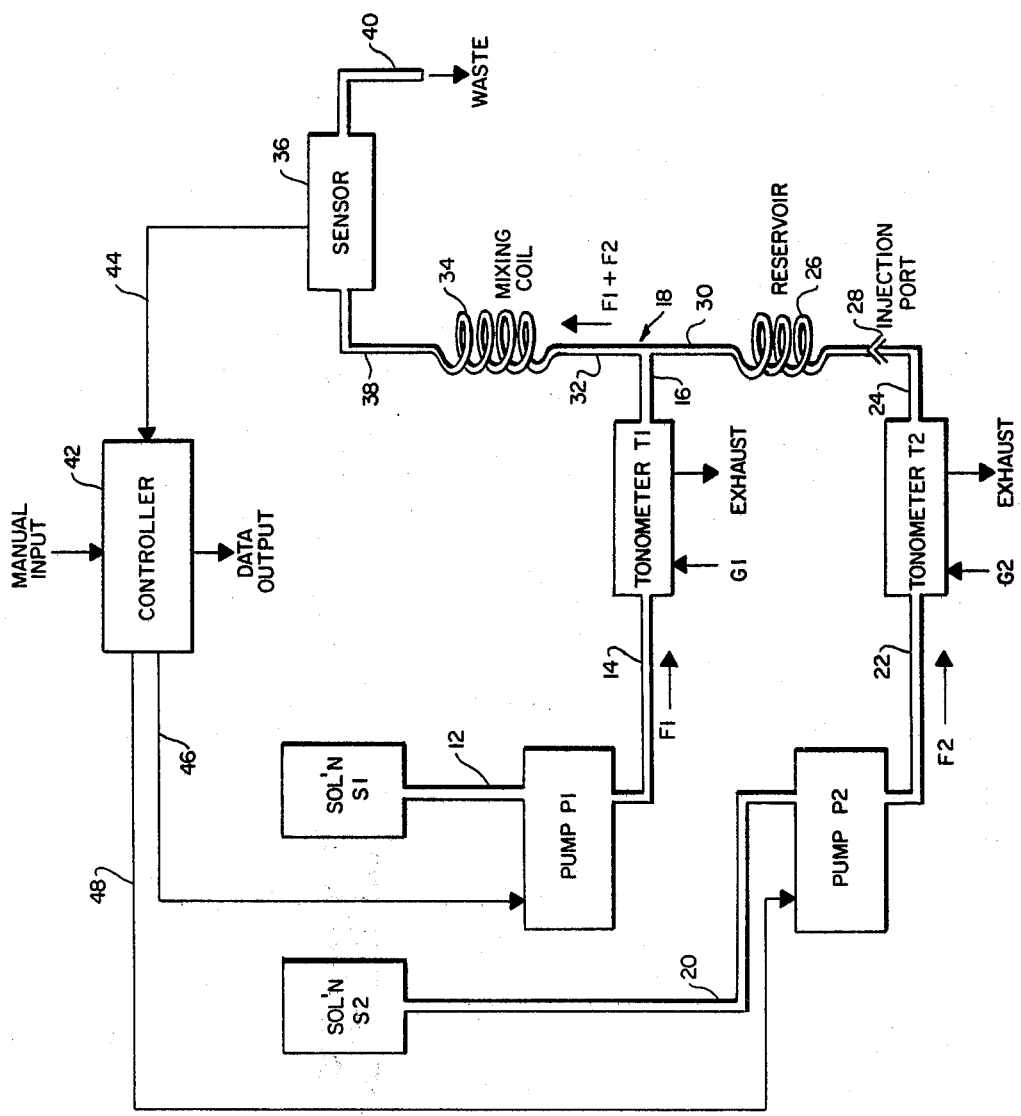
FIG. 1 depicts a generalized block diagram of the present invention.

The principle of the present measurement method, as well as the basic appartus or system required to implement the method, are illustrated in the generalized block diagram of FIG. 1. A suitable solution S1 is connected to a pump P1 via a tube or line 12. The pump P1, in turn, is similarly coupled to a tonometer T1 via line 14. The output of the tonometer T1 is likewise connected through a suitable line 16 to one port of a junction tee, shown at 18.

A second solution S2 is in fluid connection with a second pump P2 via tube or line 20. Pump P2 is then connected to a tonometer T2 with line 22. The output of the tonometer T2 is connected via line 24 to a fluid reservoir 26. Advantageously, the reservoir 26 may be realized with a suitable length of tubing that has been coiled in order to maintain it in a small area, which small area prevents cell sedimentation. An injection port 28 is interposed in the line 24 between the tonometer T2 and the reservoir 26 so as to facilitate the injecting of a blood sample, or other type of sample, whose gaseous content is to be determined, into the reservoir 26. The output of the reservoir 26 is connected with line 30 to the other input port of the junction tee 18.

The output of the junction tee 18 is then connected with tubing or line 32 to a mixing coil 34. In turn, the output of the mixing coil 34 is connected to a suitable sensor 36 with tubing or line 38. The sensor 36 has tubing 40 connected to the output thereof to allow the fluid passing therethrough to be suitably expelled to an appropriate waste station.

The sensor 36 may be a conventional polarographic sensor adapted to sense the presence of a specific gas, such as oxygen. Such sensors comprise a suitable electrode that is exposed to the fluid medium or matrix in which the gas to be measured has been physically dissolved. The current flowing from the electrode to a reference electrode gives an indication of the amount of gas that has been dissolved in the solution that is passing through the sensor. Such sensors are well known in the art and can be readily utilized by those skilled in the art in order to carry out the desired sensing functions associated with the present invention.

The sensor 36 is coupled to a suitable controller 42 over signal line 44. That is, the controller 42 receives information over signal line 44 that indicates the presence and concentration of the particular gas being sensed. The controller 42 also controls pumps P1 and P2 with appropriate control signals sent to these pumps over signal lines 46 and 48 respectively. Both pumps P1 and P2 are adapted to anaerobically pump a solution at a selected flow rate. These flow rates are represented in FIG. 1 by the arrows labeled F1 and F2. Both of these volumetric flow rates F1 and F2 are selectively adjustable under control of the controller 42.

The tonometers T1 and T2 may be of the type described in U.S. Pat. No. 4,221,567, especially the text and figures relating to items 18 and 19 thereof. It is noted that one of the inventors of that patent is the same as one of the inventors of this invention. The appropriate parts of U.S. Pat. No. 4,221,567 relating to the construction and operation of the devices 18 and 19 are hereby incorporated in this application by reference.

The function of the tonometers T1 and T2 is to provide a means whereby a desired gas, labeled G1 and G2 in FIG. 1, may by physically dissolved in a suitable solution of fluid matrix to the point of equilibrium. Thus, for example, the solution S1 which is pumped through tonometer T1 at a volumetric fluid flow rate of F1 is equilibrated with gas G1 as it exits the tonometer T1 in line 16. Similarly, the solution S2 that is pumped through tonometer T2 at the volumetric flow rate F2 is equilibrated with the gas G2 as it exits the tonometer T2 in line 24. Suitable ports are provided into and out of the tonometers T1 and T2 for allowing the desired gas to be injected thereinto and for allowing gas exhausts to be expelled therefrom.

In operation, a fluid sample (such as a blood sample) whose gaseous content is to be measured is injected into the reservoir 26 via injection port 28. This fluid sample is then pushed out of the reservoir 26 through the line 30 into the mixing tee 18 at a flow rate F2 by energizing the pump P2. This action causes the solution S2 to push the injected sample out of the reservoir 26 as above described at the volumetric flow rate F2 determined by the pump P2.

Concurrent with the pumping of the injected sample into the mixing tee 18 at the volumetric flow rate F2 is the pumping of the equilibrated solution S1 (equilibrated with gas G1) into the other port of the mixing tee 18 at the flow rate F1. The ratio of the G1 equilibrated solution S1 to the injected sample is thus equal to the ratio of F1 to F2. This ratio is appropriately selected so as to force G2 into the dissolved phase of the mixture, and to provide optimum performance of the sensor 36. For example, if the solution S1 is a saline solution, and the injected sample is a blood sample, the ratio of saline to blood may be selected to be about 30 to 1.

The mixture of the G1 equilibrated solution with the injected sample passes through the mixing coil 34, which coil insures a thorough and complete mixing of the two solutions. The mixture then flows into the sensor 36 at a volumetric flow rate equal to F1 plus F2. The gas G1 is selected to be a gas other than the gas whose presence is to be measured in the injected sample. Gas G1 may also contain a chemical property that releases the gas to be measured into the dissolved phase of the mixture (as in the case of oxygen, or $O_2$). Thus, the sensor 36, which is specifically adapted only to sense the presence of the desired gas, will respond only to any such gas that is present in the injected sample, and a signal indicating the presence and concentration of this gas is sent to the controller 42.

The sensitivity of the sensor 36 is normally dependent upon the volumetric flow rate of the fluid passing therethrough. Hence, the reading obtained over signal line 44 as the injected sample (mixed with the G1 equilibrated solution) is meaningful only to the extent that the flow rate through the sensor is known and controlled. Advantageously, this flow rate is precisely known for the method herein described. It is simply the sum of the individual flow rates F1 plus F2, which flow rates are controlled by the controller 42.

As is evident from the above description, the injected sample of fluid whose gaseous content is to be measured, mixed with the G1 equilibrated solution S1, is present in the sensor 36 for only a finite period of time. That is, only a finite amount of the sample is injected into the reservoir 36, at which time the injection port is closed and the injected sample, of whatever quantity it may be, is merely pushed through the system. In order to eliminate errors that may be associated with contaminations at the front end or rear end of this sample (or the mixture of the sample with the G1 equilibrated solution) only the sensor response from the middle portion of the mixture is received and stored at the controller 42.

After the sensor response from the middle portion of the mixture of the injected sample and the G1 equilibrated solution has been obtained as above described, the sensor 36, mixing coil 34, junction tee 18, and reservoir 26, are thoroughly flushed of all remnants of the injected sample. This flushing is accomplished by simply allowing the pump P2 to continue to pump the solution S2 through the system. As this is done, the solution S2 is equilibrated with the gas G2 in tonometer T2. This gas G2 is selected to be the same as the gas that is measured by the sensor 36. Thus, for example, where the gas to be measured is oxygen, the gas G2 is also oxygen. Thus, after the system has been flushed of all remnants of the injected sample, a mixture is formed at the junction tee 18 that comprises the G1 equilibrated solution S1 mixed with the G2 equilibrated solution S2. The ratio of the solution S1 to S2 in this mixture is simply the ratio of the flow rates F1 to F2. As this mixture of solutions S1 and S2 passes through the sensor 36, the sensor senses the presence of the G2 gas that has been equilibrated within the mixture. The controller 42 then selectively adjusts the flow rates F1 and F2 until the sensor response is the same as that previously obtained from the mixture of the injected sample with the G1 equilibrated solution. As the controller 42 adjusts the flow rates F1 and F2, it may advantageously keep the sum of these flow rates constant and equal to the combined flow rate that was used with the injected sample/G1 equilibrated solution mixture. This may be especially important if the particular sensor 36 that is used is sensitive to the flow associated with the fluid flowing therethrough, and an equal sensor response is to be obtained.

Once the sensor response to the S1/S2 mixture has been made the same as that obtained to the S1/injected sample mixture, the gaseous content of the gas G2 in the injected sample is found by performing a calculation. This gaseous content will be the same as the G2 content of the S1/S2 mixture. In turn, the gaseous content of the S1/S2 mixture is simply proportional to the ratio of the respective flow rates F1 and F2. That is, because the solution S1 is equilibrated with the gas G1 (which insures that there is 0% of the gas G2 present in the solution S1), and because the solution S2 is equilibrated with the gas G2 (which means that the solution S2 contains 100% of the gas G2 dissolved therein), the amount of gas G2 present in the S1/S2 solution is simply proportional to the ratio of the amount of solution S2 in this mixture to the amount of solution S1. This ratio, as above described, may be readily determined from the flow rates F1 and F2.

The operation of the system shown in FIG. 1 will now be explained as it could be used for a specific measurement of determining the oxygen content of blood. In the configuration shown in FIG. 1, blood is pushed anaerobically by pump P2 past the junction tee 18 after having been placed in the blood reservoir 26 at the injection port 28. The solution S1 is selected to be a saline (or a ferricyanide) solution. The gas G1 is selected to be carbon monoxide, or CO. The saline solution S1 is pushed through tonometer T1 (where CO equilibration occurs) and past the junction tee 18 where mixing with the blood takes place prior to entering the sensor 36. The sensor 36 is selected to be an oxygen sensor. The sensor response to the blood/saline mixture corresponding to the middle portion of the blood sample (avoiding end contaminations) is stored by the controller 42. The controller 42 then proceeds to prepare a saline sample that produces the same sensor response as that produced by the blood/saline mixture. In order to accomplish this task, the solution S2 is likewise selected to be a saline solution which is equilibrated with oxygen, $O_2$, in tonometer T2. The controller 42 adjusts the pump flows F1 and F2 to provide the appropriate ratio of $O_2$-equilibrated saline (100% $O_2$ from tonometer T2) and CO-equilibrated saline (0% $O_2$ from tonometer T1) under the constraint of maintaining the total flow (F1+F2) through the sensor 36 constant. As indicated above, this precaution is taken to assure that for a given oxygen pressure or tension, the response of the sensor to both solutions is identical.

Typically, the ratio of blood to saline S1 will be 1 to 30. The ratio of the saline solutions S1 to S2 will, of course, be a function of the flow rates F1 and F2 that are required in order to give a sensor response indistinguishable from the 1/30 blood saline solution.

Applying a mass balance of oxygen, the oxygen content of the blood sample is given by $$C_{O_2} = (\lambda/7.6) P_{O_2}(F1+F2)/F2 \tag{1}$$

where $C_{O_2}$ is the oxygen content of the blood, $\lambda$ is the Bunson oxygen solubility coefficient of the blood/saline mixture, $PO_2$ is the oxygen tension of the blood/saline mixture, and F1 and F2 are the flow rates associated with pumps P1 and P2 respectively during the blood/-saline mixing process.

At the null condition (that is, at the condition where the sensor 36 response to the S1/S2 saline mixture is the same as the sensor response to the blood/saline mixture), the $PO_2$ value is given by equation (2) as follows:

$$PO_2 = \frac{F2'}{F1' + F2'} (BP - 47) \qquad (2)$$

where F1' and F2' are the respective flow rates of pumps P1 and P2 at the null condition, and BP is the barometric pressure.

Substituting equation (2) into equation (1) and applying the constraint that F1 plus F2 equals F1' plus F2', $$C_{O_2} = \lambda \frac{F2'}{F2} (BP - 47)/7.6 \qquad (3)$$

Of particular interest to the objectives of the present invention, it will now be shown that equation (3) involves only physical measurements and physical constants, thereby indicating that the measurement method herein described is entitled to first principle status. The flow rates F2' and F2 and the barometric pressure BP are physical measurements that can be determined to the accuracy required by the oxygen content measurement. The oxygen solubility $\lambda$ of the blood/saline mixture (with the presence of the dissolved CO) contains two physical constants—flow rates and salt concentrations. These physical constants, in turn, determine the value of $\lambda$ to an accuracy required by any practical oxygen content measurement. The relationship between $\lambda$ and these physical constants is expressed as $$\lambda = \lambda_w(1 - \delta C)\left[1 - \left(\frac{F2}{F1 + F2}\right)(1 - R_{bs})\right] \qquad (4)$$

where $\lambda_w$ is the Bunson oxygen solubility of water at 37° C. (a physical constant); $\delta$ is the fractional oxygen depression coefficient for NaCl in water at 37° C. (also a physical constant); C is the NaCl concentration in moles; and $R_{bs}$ is the ratio of the $O_2$ solubility of blood (without $O_2$ hemoglobin binding) to the oxygen solubility of saline. The ratio of $R_{bs}$ for human blood is so close to unity (0.98) that a flow ratio F2/(F1+F2) equal to 1/30 or less insures that this term in equation (4) can be neglected. (It is to be noted that neglecting the term $[F2/(F1+F2)](1-R_{bs})$ affects equation (4) by less than 0.06%.) Therefore, eliminating this term from equation (4) and substituting what is left into equation (3) provides the final equation for calculating the oxygen content:

$$C_{O_2} = \lambda_w(1 - \delta C)\frac{F2'}{F2}\left(\frac{BP - 47}{7.6}\right) \qquad (5)$$

Thus, equation (5) shows that the oxygen content measurement is determined by the physical contents $\lambda_w$ and $\delta$ as well as the fundamental measurements of flow, barometric pressure, and knowledge of the salt concentrations of the saline diluent (the solutions S1 and S2). Therefore, the measurement is dependent only upon physical measurements and constants, as required for first principle status.

As above described, it is apparent that the method requires no standards for calibration, even though the method uses an oxygen sensor, or other appropriate sensor 36, which is a relative measuring device. This result is produced, of course, because the sensor 36 is used only as a null indicator. Comparisons are made between the solution which requires measurement and a nearly identical solution whose oxygen tension (or other gaseous tension) is modified until the null condition is achieved. The value of the gas tension required to produce the null condition is determined accurately by flow proportioning, which flow proportioning is a physical measurement which may be accurately monitored and controlled. Thus, the principle requires that the gas tensions of both solutions be identical at the null point, a condition which is assured by the flow control and chemical composition of the nulling solution (the S1/S2 mixture). This expectation has been verified experimentally.

Advantageously, the controller 42 may be realized with a microprocessor. Such a device is easily programmed to record the sensor response and to selectively control the flow rates F1 and F2 of the pumps P1 and P2 respectively.

Of course, another advantage of using a microprocessor as the controller 42 is that the microprocessor hardware is standard and quite inexpensive and readily available. Further, software support can be readily generated by those skilled in the art.

The pumps P1 and P2 are preferably realized using a stepper motor controlled syringe pump, which pumps are commercially available. Such pumps can accurately control the volumetric fluid flow in an anaerobic environment. Further, for the application illustrated in FIG. 3 (to be discussed below) such pumps are ideally suited for reversing the flow direction through the tonometer.

Figure 2:
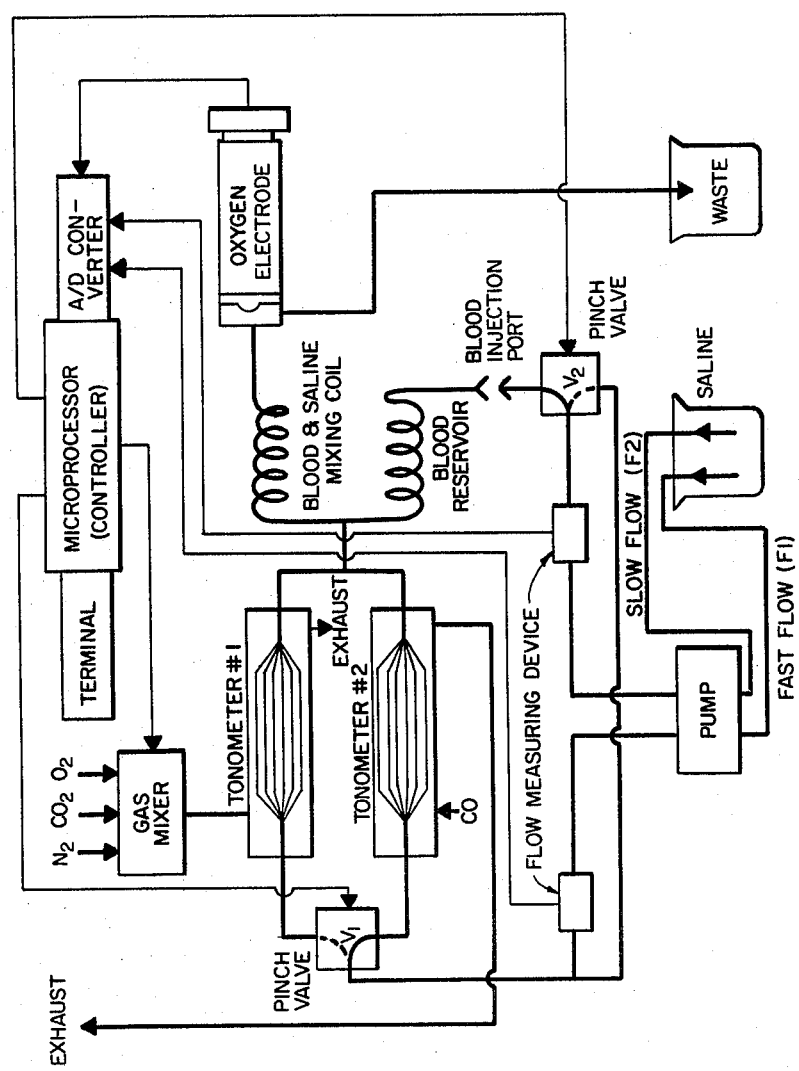
FIG. 2 shows a block diagram of a system that has been used to test the method of the present invention.

FIG. 2 illustrates a system that was used by the inventors hereof to initially demonstrate and validate the method proposed in this application. In principle, the method used with the system of FIG. 2 is the same. The apparatus and equipment used differs from FIG. 1, but the function served by the equipment are the same.

The tonometers utilized in FIG. 2 were comprised of six parallel Silastic tubes (0.025" O.D.×0.012" I.D.×25" length) contained in aluminum enclosures. Tonometer 1 was connected to the gas mixer and tonometer 2 was connected to a source of CO gas. The blood reservoir and mixing coils were constructed from nylon tubing (0.031" I.D.×0.065" O.D.). The reservoir had a volume of 0.15 ml; and the mixing coil had a volume of 0.3 ml.

The oxygen sensor was a commercial electrode (Technicon PN041-13039) housed in a stainless steel cuvette for efficient temperature control. The oxygen electrode, cuvette, mixing coil, and both tonometers are temperature controlled to 37±0.1° C. The microprocessor is a Z80 based system with a 12 bit A/D converter and CRT keyboard terminal.

While the above devices were used in connection with the configuration of FIG. 2, the same or equivalent equipment could be used in connection with the preferred configuration of FIG. 1.

The operation of the system shown in FIG. 2, which operation is similar to the operation that would be used in connection with FIG. 1, is as follows. When the unit is first turned on, a 2 point electrode calibration cycle is used to initialize the system. This consists of microprocessor controlled electrode calibration with CO equilibrated saline, followed by a calibration with saline equilibrated with a 30% oxygen gas mixture. Both slope and intercept calibration constants are calculated and stored based upon the known concentrations of these solutions. The CO saturated saline is provided by tonometer #2 (valve V1 not energized) and the 30% $O_2$ saturated saline is provided by tonometer #1 (valve V1 energized) with the gas mixer set to deliver a 30% oxygen gas mixture. Valve V2 is energized in each case to provide the same total flow condition in the electrode oxygen sensor which exists during blood content measurement. Entering the barometric pressure completes the initialization procedure, which is normally done once a day.

With the saline inlet to the blood injection port disconnected, a blood content measurement is initiated by manually injecting 0.4 ml. of blood into the blood reservoir, followed by reconnection of the saline inlet to the blood injection port. From this point on, the analysis process is automatic. Blood is slowly and continuously driven into the mixing coil at the rate F2 (0.08 ml/min) where it is mixed continuously with CO-equilibrated saline which enters the mixing coil from tonometer #2 at the faster rate F1 (2.4 ml/min). The mixing coil provides uniform mixing of blood and saline and sufficient time to insure displacement (by CO) of virtually all combined oxygen from hemoglobin to the dissolved phase prior to reaching the oxygen sensor. The initial and final quarters of the blood/saline mixture which arrive at the electrode are ignored to avoid contamination errors. However, the electrode output during the time the middle half of the mixture is in the electrode is received and averaged by the microprocessor. An estimate of the oxygen tension of the blood/saline mixture is computed from the average electrode value and the calibration data previously stored in the system.

The nulling processes are initiated by setting the gas mixer to provide a gas mixture which contains the same oxygen partial pressure as the oxygen tension estimate. Valves V1 and V2 are then energized in order to cause saline, equilibrated at this oxygen tension, to enter the oxygen electrode with the same flow conditions as the previous blood/saline mixture. The output of the oxygen electrode from the tonometered saline solution is now used as a new calibration point (close to the blood/saline tension value) for recalibrating the slope calibration parameter. Using the new slope parameter, the oxygen tension of the blood/saline mixture is recalibrated. The electrode voltage difference corresponding to the new calibration point at the blood/saline mixture is checked against a predetermined value. If the absolute magnitude of this difference is greater than the value, the gas mixer is reset to the latest calculated value of the blood/saline oxygen tension and the cycle is repeated until the oxygen tension of the saline from tonometer #1 sufficiently matches the oxygen of the blood/saline mixture to meet the accuracy criteria of the system.

After a match as above described is achieved, the oxygen content of the blood sample is computed from the appropriate equation using the latest calibrated value (null value) of the blood/saline oxygen tension.

The oxygen content is printed or otherwise outputted or displayed from the microprocessor. The system then completes a blood washout in preparation for the next blood sample.

The accuracy criteria is set by the operator by entering a percent error limit into the system. With normal electrode function, no more than two cycles are required to provide a measurement having a systematic error which falls within the precision limits of the system. However, only one cycle is normally required to meet this accuracy criteria. For this usual situation, the total measurement and washout time equals about 4.5 minutes.

The advantages of the method and system herein described over the Van Slyke and other prior art methods include (1) a design simplicity which lends itself to microprocessor control; (2) operator independent accuracy and decision; (3) reduced measurement time; and (4) smaller sample size (which can be scaled down much further than has been done to date). However, the Van Slyke method has the inherent capability to measure contents of any blood gas for which chemical means exist to selectively remove the gas from all the gas components. To achieve this same purpose, the method herein described requires an electrode which is specific to each particular blood gas whose content is to be measured. However, in practice, there is only one gas of interest other than oxygen as far as blood gases are concerned. That gas is carbon dioxide. An electrode specific to dissolve carbon dioxide is commonly available. To effectively determine carbon dioxide at a $CO_2$ specific electrode, it is preferable that the saline solutions being utilized should be buffered at a sufficiently low or acid pH to drive essentially all of the carbon dioxide in the samples and in the equilibrated diluents into the dissolved state. Thus, an expanded system could be devised, as shown in FIG. 3, wherein both the oxygen and carbon dioxide contents could be determined, as explained more fully below.

Advantageously, the flow proportioning method herein described achieves an accuracy that the inherent is equal to or exceeds that of Van Slyke.

Figure 3:
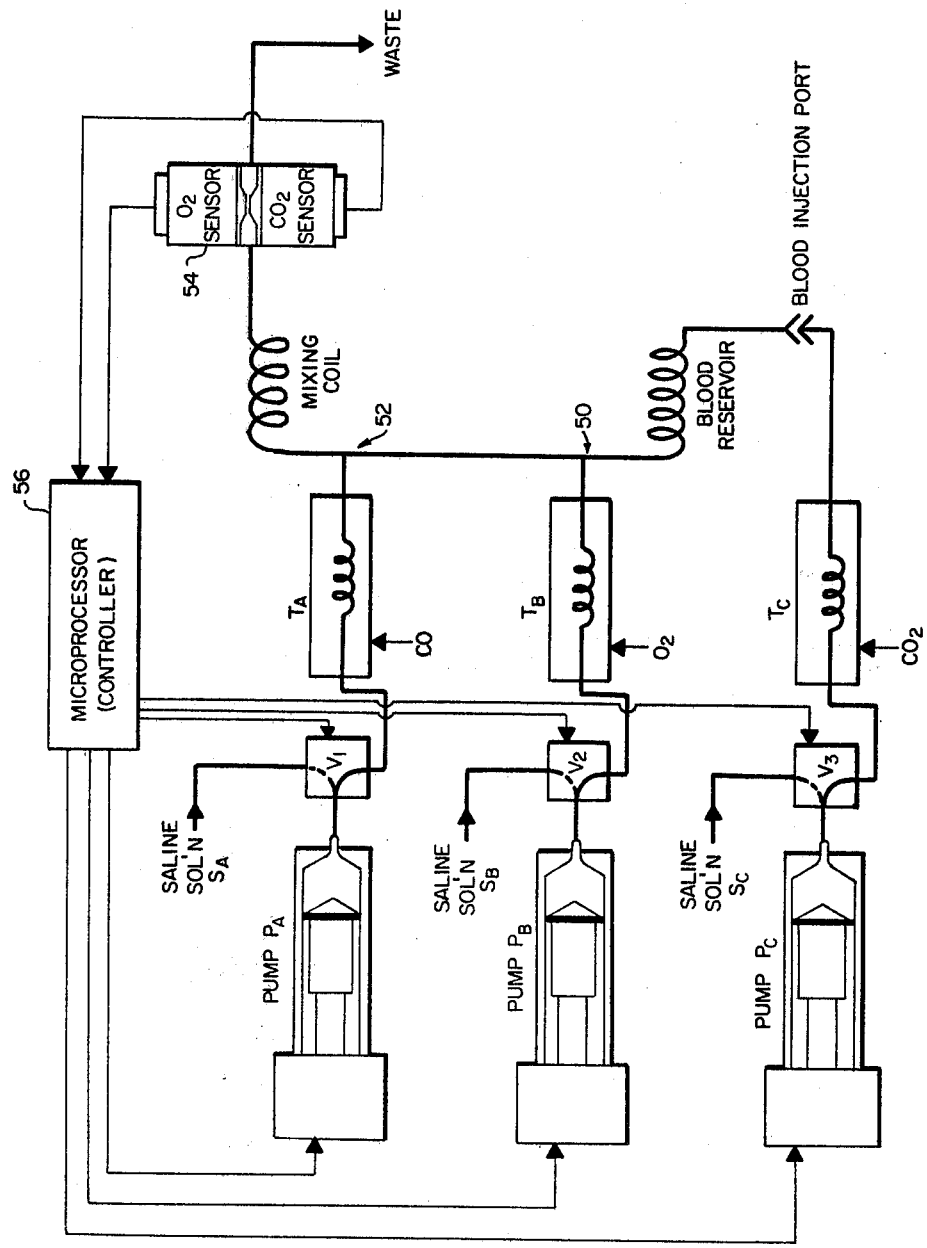
FIG. 3 illustrates a block diagram of an expanded embodiment of the present invention that is used to determine a plurality of measurements, such as the oxygen content, carbon dioxide content, oxygen capacity, hemoglobin, and oxygen saturation of a blood sample, in a single measurement process.

The system shown in FIG. 3 is an extension of the basic system shown in FIG. 1. Three pumps, $P_A$, $P_B$, and $P_C$ are used with three tonometers, $T_A$, $T_B$, and $T_C$. A first mixing tee, shown at 50, connects the output of the blood reservoir to one end of the tonometer $T_B$. A second mixing tee, shown at 52, connects the output from the mixing tee 50 to one end of the tonometer $T_A$. A dual sensor 54 is employed which includes an oxygen electrode and a carbon dioxide electrode. Both of these electrodes are coupled to the microprocessor or controller 56. The microprocessor also controls, as is the case with the basic system of FIG. 1, the pumps $P_A$, $P_B$, and $P_C$, as well as the valves $V_1$, $V_2$, and $V_3$. The valves $V_1$, $V_2$ and $V_3$ are used to permit the stepper motor controlled syringe pumps $P_A$, $P_B$, and $P_C$ to be filled with appropriate saline solutions $S_A$, $S_B$, and $S_C$ as needed.

In operation, blood is first pushed anaerobically by pump $P_C$ past the junction tee 50 of tonometer $T_B$ while pump $P_B$, at a rate one half that of pump $P_C$, splits the blood sample by pulling half of the sample into tonometer $T_B$. The remaining half of the sample is pushed past the junction tee 52 of tonometer $T_A$ where it is mixed with CO equilibrated saline from tonometer $T_A$ in the mixing coil at a proportion of about one part blood to thirty parts of saline. The blood/saline mixture proceed to the sensor cuvette 54. The averages of the oxygen and carbon dioxide sensors (corresponding to the middle half of the sample to eliminate any contaminations) are stored in the microprocessor. At this point, a duplicate sample of blood has been received by tonometer $T_B$ and equilibrated with oxygen for use for measurement of oxygen capacity.

Next, pump $P_C$ is stopped and pump $P_B$ receives and pushes the blood contents of tonometer $T_B$ by the junction tee 52 at the same rate as done previously by pump $P_C$, and the same process of mixing, measurement, and data storage is performed for the second half of the split blood sample.

The next sequence of the method determines the $O_2$ and $CO_2$ tensions of the previous two blood/saline mixes (necessary to determine their gas contents) by producing saline mixtures in the mixing coil which match the $O_2$ and $CO_2$ tensions of the previous blood/saline mixtures. This is done by performing a rapid cleanout of blood from the reservoir, and by adjusting the flow rates of the three pumps by the microprocessor using a simple feedback control algorithm until the mixed saline sample producing the same electrical outputs of each sensor as was produced by the first blood/saline mixture. The same process is then repeated until a match is produced for the second blood/saline mixture. During this matching process, the sum of all the pump flows are constrained to equal the total flow of the blood/saline mixture in order to avoid differences in sensor responses due to flow artifacts and the like.

Applying mass balance of oxygen and carbon dioxide to the first blood/saline mixture, the following relationships are found:

$$C_{O2} = \lambda_{O2} \frac{F_{O2}}{F_B} (BP - 47)/7.6 \tag{6}$$

$$C_{CO2} = \lambda_{CO2} \frac{F_{CO2}}{F_B} (BP - 47)/7.6 \tag{7}$$

where $C_{O2}$ and $C_{CO2}$ represent oxygen and carbon dioxide content respectively of the blood, in units of volume percent; $\lambda_{O2}$ and $\lambda_{CO2}$ represent their respective gas solubilities of the diluent at 37° C.; $F_B$ is the blood flow; $F_{O2}$ and $F_{CO2}$ represent the respective flows of pumps $P_B$ and $P_C$ required to obtain the null conditions with the first blood/saline mixture, and $B_P$ is the barometric pressure in mm of Hg.

Applying mass balance of oxygen to the second blood/saline mixture, $$\text{Oxygen Capacity} = \lambda_{O2} \left( \frac{F_{O2}'}{F_B} - 1 \right) (BP - 47)/7.6 \tag{8}$$

where $F_{O2}'$ represents the flow of pump $P_B$ required to obtain the null condition.

The value of hemoglobin available for gas exchange is then given by $$Hb = (O_2 \text{ capacity} - 0.003 (BP-47))/1.39 \tag{9}$$

where Hb represents the hemoglobin available.

Finally, oxygen saturation, defined as the ratio of oxyhemoglobin available for gas exchange, and represented by the symbol $S_{O2}$, is given by $$S_{O2} = (C_{O2} - 0.003 \, PO_{2s})/(1.39 \, Hb) \tag{10}$$

where $PO_{2s}$ is the value of $PO_2$ from the standard oxyhemoglobin dissociation curve corresponding to the calculated value of oxygen saturation. Thus, equation (10) requires an iterative solution which is performed by the microprocessor. The maximum uncertainty of $S_{O2}$ due to the estimate of $PO_{2s}$ is less than 1% in the normal physiological range.

While the invention herein disclosed has been described by means of specific embodiments and applications thereof, numerous modifications and variations could be made thereto by those skilled in the art without departing from the spirit and scope of the present invention. It is therefore to be understood that within the scope of the appended claims, the invention may be practiced otherwise than as specifically described herein.

What is claimed is:

1. A method for determining the oxygen content of blood comprising the steps of:
    (a) preparing a first saline solution having carbon monoxide gas absorbed therein to a point of equilibrium;
    (b) injecting a sample of blood whose oxygen content is to be measured into a blood reservoir;
    (c) mixing said first equilibrated saline solution with said blood sample by:
        (1) causing said first saline solution to flow into a first inlet port of a mixing tee at a first fixed volumetric flow rate,
        (2) causing said blood sample to flow into a second inlet port of said mixing tee at a second fixed volumetric flow rate, and
        (3) directing an output port of said mixing tee to a mixing coil wherein said first saline solution and said blood sample are mixed together to form a blood/saline mixture;
    (d) causing said blood/saline mixture to flow through an oxygen sensor at a third fixed volumetric flow rate, said third fixed flow rate being determined by the sum of said first and second fixed volumetric flow rates;
    (e) recording the measured response of said oxygen sensor to the blood/saline mixture passed therethrough;
    (f) preparing a second saline solution having oxygen absorbed therein to a point of equilibrium; ;p1 (g) mixing said first and second saline solutions together by:
        (1) causing said first saline solution to flow into the first inlet port of said mixing tee at a first controlled volumetric flow rate,
        (2) causing said second saline solution to flow into the second inlet port of said mixing tee at a second controlled volumetric flow rate, and
        (3) directing the output port of said mixing tee to said mixing coil wherein said first and second saline solutions are mixed together to form a saline mixture;
    (h) causing said saline mixture to flow through said oxygen sensor at the same third fixed volumetric flow rate as in step (d), said third fixed flow rate being determined by the sum of said first and second controlled volumetric flow rates;
    (i) selectively adjusting said first and second controlled volumetric flow rates while maintaining said third fixed volumetric flow rate until the response of said oxygen sensor to said saline mixture flowing therethrough is within a predetermined tolerance of the response of said oxygen sensor measured and recorded in step (e);

(j) calculating the oxygen content of said saline mixture based upon known physical measurements and constants, including the ratio of said first and second controlled volumetric flow rates arrived at in step (i); and (k) using the calculated oxygen content of said saline mixture as a relatable measure of the oxygen content of said blood sample.

2. A method as defined in claim 1 wherein steps (a) and (f) of preparing a saline solution having a gas absorbed therein to a point of equilibrium include the use of a tonometer.

3. A method as defined in claim 1 wherein the mixture of step (c) comprises a ratio of equilibrated carbon monoxide saline solution to blood of approximately 30 to 1.

4. A method as defined in claim 1 wherein the recording and comparison of the oxygen sensor response included in steps (e) and (i), the selective adjustment of said first and second volumetric flow rates of step (i), and the calculations of steps (j) and (k) are carried out under microprocessor control.

5. A method as defined in claim 4 wherein all steps except step (b) are carried out automaticaly under microprocessor control.

6. A method as defined in claim 4 wherein the volumetric flow rates associated with steps (c), (d), (g) and (h) are set by pumps in fluid connection with appropriate sources of saline solution, said pumps being adapted to pump said saline solutions at flow rates controlled by said microprocessor.

7. A method as defined in claim 6 wherein the pumps are specifically adapted to anaeobically pump said saline solutions.

8. A method for determining the gas content of a first gas dissolved in a first fluid sample comprising the steps of:

(a) preparing a first diluent having a second gas dissolved therein to a point of equilibrium;

(b) injecting a portion of said first fluid sample having said first gas dissolved therein into a reservoir;

(c) mixing said first equilibrated diluent with said first fluid sample by:
  (1) causing said first diluent to flow into a first inlet port of a mixing tee at a first volumetric flow rate,
  (2) causing said first fluid sample to flow into a second inlet port of said mixing tee at a second fixed volumetric flow rate, and
  (3) directing an output port of said mixing tee to a mixing coil wherein said first diluent and said first fluid sample are mixed together to form a first diluent/first fluid sample mixture;

(d) causing said first diluent/first fluid sample mixture to flow through a first gas sensor at a third fixed volumetric flow rate, said third fixed flow rate being determined by the sum of said first and second fixed volumetric flow rates;

(e) recording the measured reponse of said first gas sensor to the first diluent/first fluid sample mixture passed therethrough;

(f) a second diluent solution having said first gas absorbed therein to a point of equilibrated diluents together by:

(1) causing said first diluent to flow into a first inlet port of said mixing tee at a first controlled volumetric flow rate,
(2) causing said second diluent to flow into said second inlet port of said mixing tee at a second controlled volumetric flow rate, and
(3) directing the output port of said mixing tee to said mixing coil wherein said first and second diluents are mixed together to form a first diluent/second diluent mixture;

(h) causing said first diluent/second diluent mixture to flow through said first gas sensor at the same third fixed volumetric flow rate as in step (d), said third fixed flow rate being determined by the sum of said first and second controlled volumetric flow rates;

(i) selectively adjusting said first and second controlled volumetric flow rates while maintaining said third fixed volumetric flow rate until the response of said first gas sensor to said first diluent/second diluent mixture flowing therethrough is within a predetermined tolerance of the response of said first gas sensor measured and recorded in step (e);

(j) calculating the first gas content of said first diluent/second diluent mixture based upon known physical measurements and constants, including the ratio of said first and second controlled volumetric flow rates arrived at in step (i); and (k) using the calculated first gas content of said first diluent/second diluent mixture as a relatable measure of the first gas content of said first fluid sample.

9. A method as defined in claim 8 wherein the volumetric flow rates associated with each diluent are controlled by an anaerobic pump.

10. A method as defined in claim 9 further wherein said anaerobic pumps are controlled by a microprocessor.

11. A method as defined in claim 10 wherein said microprocessor is further adapted to receive and store the response of said sensor and to perform the calculations of step (j).

12. A method as defined in claim 11 wherein said second gas comprises carbon monoxide.

13. A method as defined in claim 11 wherein said first fluid sample comprises blood, said first gas comprises carbon dioxide, said first gas sensor is adapted to measure carbon dioxide, and said first and second diluents comprise buffered saline solutions buffered at a pH sufficiently low to drive essentially all of the carbon dioxide of the first diluent/second diluent mixture into the dissolved state.

14. A system for measuring the gas content of a first gas dissolved in a first fluid sample comprising:

means for preparing a second fluid sample having a second gas dissolved therein to a point of equilibrium;

means for mixing a quantity of a first fluid sample having a first gas dissolved therein with said second fluid sample to form a first mixture;

means for exposing a gas sensor to said first mixture under controlled conditions, said gas sensor being adapted to signal the amount of said first dissolved gas that has been sensed, and said controlled conditions including means for maintaining the volumetric flow rate of said first mixture at a fixed known value as it comes in contact with said sensor;

means for preparing a third fluid sample having said first gas dissolved therein to a point of equilibrium;

means for mixing said second and third fluid samples to form a second mixture;

means for exposing said gas sensor to said second mixture under controlled conditions, said controlled conditions including means for maintaining the volumetric flow rate of said second mixture at the same fixed known value as said first mixture;

means for selectively adjusting the respective proportions of said second and third fluid samples that constitute said second mixture while maintaining the volumetric flow rate at said fixed known value until a response is generated by said sensor that is approximately the same as the response of said sensor to said first mixture; and controller means signally connected in said system in such a manner as to provide for the selective mixing of said first and second fluid samples and said second and third fluid samples to form said first and second mixtures respectively, for maintaining the volumetric flow rate of said first and second mixtures, for receiving signals from said gas sensor, and for calculating the content of said first gas in said first fluid sample based upon known physical measurements and constants including volumetric flow rates.

15. A system as defined in claim 14 wherein said means for selectively adjusting the respective proportions of said second and third fluid samples within said second mixture comprises:

a junction tee;

a first conduit that couples a fluid source for said second fluid sample to a first input port of said tee;

a first pump signally connected to said controller means interposed in said first conduit for receiving fluid from said fluid source for said second fluid sample and selectively pumping it at a controlled volumetric flow rate towards said junction tee;

a second conduit that couples a fluid source for said third fluid sample to a second input port of said tee; and a second pump signally connected to said controller means interposed in said second conduit for receiving fluid from said fluid source for said third fluid sample and selectively pumping it at a controlled volumetric flow rate towards said junction tee;

whereby the proportion of said second or third fluid samples within said second mixture is proportional to the ratio of the respective flow rates associated with said second and third fluid samples to the flow rate of said second mixture.

16. A system as defined in claim 15 wherein said means for preparing said second fluid sample with said second gas dissolved therein comprises a first tonometer permeable to said second gas interposed in said first conduit between said first pump and junction tee, said first tonometer having a source of said second gas coupled thereto.

17. A system as defined in claim 16 wherein said means for preparing said third fluid sample with said first gas dissolved therein comprises a second tonometer permeable to said first gas interposed in said second conduit between said second pump and junction tee, said second tonometer having a source of first gas coupled thereto.

18. A system as defined in claim 17 wherein said means for mixing said first fluid sample with said second fluid sample comprises:

a reservoir interposed in said second conduit between said second tonometer and said junction tee, said reservoir being adapted to receive a quantity of first fluid sample;

an injection port placed in said second conduit between said tonometer and said reservoir, said injection port being adapted to allow said quantity of first fluid sample to be injected into said reservoir; and wherein said controller means is signally coupled to said first and second pumps so as to selectively energize said pumps, thereby causing said second fluid sample to flow into one input port of said junction tee at a first controlled flow rate as determined by said first pump, and said first fluid sample to flow into the other input port of said junction tee at a second controlled flow rate, said first fluid sample being pushed out of said reservoir, through said second conduit, and into said junction tee by fluid from said second fluid source, which fluid is pumped by said second pump.

19. A system as defined in claim 18 further including a mixing coil coupled to the output of said junction tee.

20. A system as defined in claim 18 wherein said means for exposing said gas sensor to said first and second mixtures under said controlled conditions includes:

an electrode sensor adapted to have said first and second mixtures come in contact therewith after said mixtures have passed through said junction tee;

means for signally connecting said electrode to said controller; and programming means within said controller for maintaining the flow rate of said mixtures at a desired rate.

21. A system for determining the chemical substances and properties of a fluid matrix comprising:

a first fluid line coupled between a first fluid source and a first port of a first mixing tee;

a second fluid line coupled between a second fluid source and a first port of a second mixing tee;

a third fluid line coupled between a third fluid source and a second port of said second mixing tee;

connection means for coupling a third port of said second mixing tee to a second port of said first mixing tee;

a sensor in fluid communication with a third port of said first mixing tee;

pumping means coupled to each of said first, second, and third fluid lines for selectively and individually controlling the volumetric flow rate of the fluids that respectively flow through said lines;

gas dissolving means coupled to each of said first, second and third fluid lines for selectively and individually dissolving a specified gas in the fluids that respectively flow through said lines to a desired concentration level;

reservoir means interposed in said third fluid line for holding and storing a quantity of fluid therein prior to introducing said fluid to the second mixing tee;

injection means for allowing a sample of a desired fluid matrix whose gaseous content and other chemical properties are to be determined to be injected into said reservoir means; and a controller coupled to said pumping means and said sensor, said controller being adapted to perform the following tasks:

selectively moving said fluid matrix sample through said first and second mixing tees, splitting said sample into at least two portions as it does so, and to selectively mix said sample portions with fluid having a specified gas dissolved therein from one of said fluid sources, thereby forming at least two sample/fluid mixtures, and for further allowing a specified gas to be dissolved into at least one portion of said fluid matrix sample prior to forming its respective sample/fluid mixture, allowing said sample/fluid mixtures to be respectively moved into fluid contact with said sensor at a controlled flow rate, recording the response of said sensor to its contact with said sample/fluid mixtures, selectively controlling said pumping means so as to flush the system of all traces of said fluid matrix sample, selectively and sequencially preparing a plurality of fluid mixtures from said first, second and third fluid sources, said mixtures being prepared by controlling the respective flow rates of said first, second, and third fluids as said fluids flow through their respective fluid lines into the corresponding junction tees, allowing said fluid mixtures to be respectively moved into fluid contact with said sensor at the same flow rate as did said sample/fluid mixtures, selectively adjusting the flow rates associated with said first, second, or third fluids, thereby adjusting the composition of said fluid mixtures in proportion to said flow rates, the flow rate of said fluid mixtures when exposed to said sensor being maintained constant, until the response of said sensor to a specific fluid mixture is the same as the response of said sensor to a specific sample/fluid mixture, and calculating the gaseous content and other properties of the fluid matrix sample based upon known physical measurements and constants including flow rates of the fluids.

22. A system as defined in claim 21 wherein said pumping means comprise first, second and third stepper motor controlled syringe pumps coupled respectively to said first, second, and third fluid lines.

23. A system as defined in claim 22 further including first, second, and third valve means coupled respectively to said first, second, and third stepper motor syringe pumps, each of said valve means being adapted to allow fluid to enter into the syringe portion of said pumps from the respective first, second, or third fluid sources, or to allow fluid to be pumped out of the syringe portion of said pumps towards said mixing tees under control of said controller.

24. A system as defined in claim 21 wherein said gas dissolving means comprise first, second, and third tonometers coupled respectively to said first, second and third fluid lines.

25. A system as defined in claim 24 wherein said first, second, and third fluid sources each comprise a source of buffered saline solution having a low pH.

26. A system as defined in claim 24 wherein the first tonometer is permeable to carbon monoxide, the second tonometer is permeable to oxygen, and the third tonometer is permeable to carbon dioxide.

27. A system as defined in claim 26 wherein said sensor includes two separate gas sensitive electrodes, one of which is adapted to be sensitive to oxygen, and the other of which is adapted to be sensitive to carbon dioxide.

* * * * *